(12) United States Patent
Si et al.

(10) Patent No.: US 7,141,607 B1
(45) Date of Patent: Nov. 28, 2006

(54) METHODS AND COMPOSITIONS FOR TREATING AND INHIBITING RETINAL NEOVASCULARIZATION

(75) Inventors: Erwin Si, Alameda, CA (US); Lyle M. Bowman, Pleasanton, CA (US)

(73) Assignee: Insite Vision Incorporated, Alameda, CA (US)

(*) Notice: Subject to any disclaimer, the term of this patent is extended or adjusted under 35 U.S.C. 154(b) by 0 days.

(21) Appl. No.: 09/523,102

(22) Filed: Mar. 10, 2000

(51) Int. Cl.
*A61K 31/215* (2006.01)
*A61K 31/74* (2006.01)

(52) U.S. Cl. .................................. 514/530; 424/78.04
(58) Field of Classification Search ............... 514/575, 514/553, 533, 532, 529, 506
See application file for complete search history.

(56) References Cited

U.S. PATENT DOCUMENTS

| | | | |
|---|---|---|---|
| 2,798,053 A | 7/1957 | Brown | |
| 4,136,250 A | 1/1979 | Mueller et al. | |
| 4,192,827 A | 3/1980 | Mueller et al. | |
| 4,548,990 A | 10/1985 | Mueller et al. | |
| 4,816,456 A | 3/1989 | Summers | |
| 5,188,826 A | 2/1993 | Chandrasekaran et al. | |
| 5,192,535 A | 3/1993 | Davis et al. | |
| 5,240,958 A | 8/1993 | Campion et al. | |
| 5,260,059 A | 11/1993 | Acott et al. | |
| 5,332,582 A | 7/1994 | Babcock et al. | |
| 5,340,572 A | 8/1994 | Patel et al. | |
| 5,538,721 A * | 7/1996 | Babcock et al. | |
| 5,684,152 A | 11/1997 | Ponpipom et al. | |
| 5,691,382 A | 11/1997 | Crimmin et al. | |
| 5,696,082 A | 12/1997 | Crimmin et al. | |
| 5,700,838 A | 12/1997 | Dickens et al. | |
| 5,763,621 A | 6/1998 | Beckett et al. | |
| 5,767,153 A * | 6/1998 | Bowman et al. | 514/530 |
| 5,801,156 A | 9/1998 | Robinson et al. | |
| 5,827,702 A | 10/1998 | Cuthbertson | |
| 5,861,436 A | 1/1999 | Beckett et al. | |
| 5,861,510 A | 1/1999 | Piscopio et al. | |
| 5,863,949 A | 1/1999 | Robinson et al. | |
| 5,866,717 A | 2/1999 | Beckett et al. | |
| 5,872,152 A | 2/1999 | Brown et al. | |
| 5,876,744 A | 3/1999 | Della Valle et al. | |
| 5,902,791 A | 5/1999 | Beckett et al. | |
| 5,917,090 A | 6/1999 | Huxley et al. | |
| 5,925,637 A | 7/1999 | VanZandt et al. | |
| 5,929,097 A | 7/1999 | Levin et al. | |
| 5,932,572 A | 8/1999 | Dean et al. | |
| 5,932,695 A | 8/1999 | Floyd et al. | |
| 6,017,949 A * | 1/2000 | D'Amato et al. | |
| 6,239,113 B1 | 5/2001 | Dawson et al. | |
| 6,375,963 B1 | 4/2002 | Repka et al. | |
| 6,378,526 B1 * | 4/2002 | Bowman et al. | 128/898 |
| 6,455,283 B1 | 9/2002 | Ferrara et al. | |

| | | |
|---|---|---|
| 2002/0032315 A1 | 3/2002 | Baca et al. |

FOREIGN PATENT DOCUMENTS

| | | |
|---|---|---|
| EP | 0312208 | 9/1988 |
| EP | 0 895 988 A1 | 2/1999 |
| EP | 0 930 067 A2 | 7/1999 |
| EP | 1040837 A2 | 10/2000 |
| WO | WO 9529696 A1 | 11/1995 |
| WO | WO 9603985 A1 | 2/1996 |
| WO | WO 97/18835 | 5/1997 |
| WO | WO 97/43245 | 11/1997 |
| WO | WO 97/43247 | 11/1997 |
| WO | WO 9741844 A1 | 11/1997 |
| WO | WO 98/07697 | 2/1998 |
| WO | WO 98/09940 | 3/1998 |
| WO | WO 98/12211 | 3/1998 |
| WO | WO 9810758 A1 | 3/1998 |
| WO | WO 98/16520 | 4/1998 |
| WO | WO 98/33768 | 8/1998 |
| WO | WO 9913909 A1 | 3/1999 |
| WO | WO 99/19296 | 4/1999 |
| WO | WO99/22713 | 5/1999 |
| WO | WO 9945929 A1 | 9/1999 |
| WO | WO-9958126 * | 11/1999 |
| WO | WO-007565 * | 2/2000 |
| WO | WO 0007565 A2 | 2/2000 |
| WO | WO 0007565 A3 | 2/2000 |
| WO | WO 00/40089 | 7/2000 |

OTHER PUBLICATIONS

Ricci et al., "Oxygen-induced retinopathy in the newborn rat: effects of hyperbarism and topical administration of timolol maleate", Graefe's Archive for Clinical and Experimental Ophthalmology 233 (4) : 226-30 (1995).*
MedlinePlus Medical Dictionary definition of pterygium.*
MedlinePlus Medical Dictionary definition of prophylaxis.*
ARVO Abstract Book, Annual Meeting Fort Lauderdale, Florida May 9-14, 1999, IOVS, Mar. 1999, vol. 40, No. 4, p. S231.
Arup Das, et al., *Human Diabetic Neovascular Membranes Contain High Levels of Urokinase and Metalloprotinase Enzymes*, IOVS, Mar. 1999, vol. 40, No. 3, 809-813.

(Continued)

*Primary Examiner*—Sandra E. Saucier
(74) *Attorney, Agent, or Firm*—McDermott Will & Emery LLP

(57) ABSTRACT

Methods and compositions for the prophylactic and therapeutic treatment of retinal disorders associated with neovascularization using topical ophthalmic compositions comprising hydroxamic acid matrix metalloproteinase inhibitors such as batimastat.

43 Claims, 5 Drawing Sheets

OTHER PUBLICATIONS

Arup Das, et al., *Retinal Neovascularization Is Suppressed With a Matrix Metalloproteinase Inhibitor*, Archive of Ophthalmology, vol. 117, No. 4, Apr. 1999, 498-503.

Joseph Frucht-Pery, MD, et al., *Topical Indomethacin Solution Versus Dexamethasone Solution for Treatment of Inflamed Pterygium and Pinguecula: A Prospective Randomized Clinical Study*, American Journal of Ophthalmology, Feb. 1999, vol. 127, 148-152.

G. A. Lutty, et al., *Nonperfusion of retina and choroid in transgenic mouse models of sickle cell disease*, Current Eye Research, vol. 17, No. 4, Apr. 1998, 438-444.

N. N. Osborne, et al., *Topically Applied Betaxolol Attenuates NMDA-induced Toxicity to Ganglion Cells and the Effects of Ischaemia to the Retina*, Exp. Eye Res. (1999) 69, 331-342.

Gholam A. Peyman, *Vitreoretinal Diseases: Pathological Aspects and Therapeutic Strategies*, Ocular Therapeutics and Drug Delivery A Multi-Disciplinary Approach, 265-266.

Lutz E. Pillunat, et al., *Effect of topical dorzolamide on optic nerve head blood flow*, Craefes Arch Clin Exp Ophthalmol (1999) 237: 495-500.

Maria Emanuel Ryan, et al., *MMP-Mediated Events in Diabetes*, Annals of the New York Academy of Sciences Vol. 878 Inhibition of Matrix Metalloproteinases Therapeutic Applications, 1999, 311-334.

Sebastian Wolf, et al., *Acute effect of metipranolol on the retinal circulation*, British Journal of Ophthalmology 1998; 82: 892-896.

Edward J. Zabawski, Jr., Do, et al., *Topical and intralesional cidofovir: A review of pharmacology and therapeutic effects*, Journal of the American Academy of Dermatology1998; 39: 741-5.

Baraldi, et al., *Synthesis, in Vitro Antiproliferative Activity, and DNA-Binding Properties of Hybrid Molecules Containing Pyrrola [2.1-c][1.4]b benzodiazepine and Minor-Groove-Binding Oligopyrrole Carriers*, Journal of Medical Chemistry 42(25): 5131-41 (1999).

Bayless, et al., *RGD-Dependent Vacuolation and Lumen Formation Observed during Endothelial Cell Morphogenesis in Three-Dimensional Fibrin Matrices Involves the $a_vB_3$ and $a_5B_1$ Integrins*, American Journal of Pathology 156(5): 1673-83 (2000).

Bevilacqua, et al., *Recent Contributions to Knowledge of the Mechanism of Action of Nimesulide*, Drugs 46 Suppl. 1: 40-47 (1993).

Bigg, et al., *Mechanisms of induction of human tissue inhibitor of metalloproteinases-1 (TIMP-1) gene expression by all-trans retinoic acid in combination with basic fibroblast growth factor*, European Journal of Biochemistry 267(13): 4150-56 (2000).

Binetruy-Tournaire, et al., *Identification of a peptide blocking vascular endothelial growth factor (VEGF)-mediated angiogenesis*, EMBO J. 19(7): 1525-33 (2000).

Campbell, et al., *Malonyl aa-Mercaptoketones and a-Mercaptoalcohols, A New Class of Matrix Metalloproteinase Inhibitors*, Bioorganic Medical Chemistry Letters 8(10): 1157-62 (1998).

Cherney, et al., *Macrocyclic Hydrozamate Inhibitors of Matrix Metalloproteinases and TNF-a Production*, Bioorganic Medical Chemistry Letters 9(9): 1279-84 (1999).

Colombo, S., et al., "An Eye Drop Form of an Extracellular Proteinase Inhibitor Prevents Retinal Neovascularization in an Animal Model," Biosciences Information Service cited as XP002183948 on the International Search Report dated Mar. 15, 2000.

Colorado, et al., Anti-angiogenic Cures From Vascular Basement Membrane Collagen, Cancer Research 69(9): 2520-26 (2000).

Coors, et al., The Investigative Ophthalmology & Visual Sciences 40(4): S231 (1999).

Dark, et al., *Combretastatin A-4, an Agent that Displays Patent and Selective Toxicity toward Tumor Vasculature*, Cancer Research 57 (10): 1829-34 (1997).

Fairbrother, et al., *Novel Peptides Selected to Bind Vascular Endothelial Growth Factor Target the Receptor-Binding Site*, Biochemistry 37(51): 17754-64 (1998).

Fife, et al., *Effects of tetracyclines on angiogenesis in vitro*, Cancer Letters: 153(1-2): 75-8 (2000).

Fini, et al., *An Inhibitor of the Matrix Metalloproteinase Synthesized*, Invest. Ophthalmol. Vis. Sci. 32(11): 2997-3001 (1991).

Floege, et al., *Novel Approach to Specific Growth Factor Inhibition in Vivo*, American Journal of Pathology 154(1): 169-79 (1999).

Gilbertson-Beadling, et al., *The tetracycline analogs minocycline and doxycycline inhibit angiogenesis in vitro by a non-metalloproteinase-dependent mechanism*, Cancer Chemother, Pharmacol. 36(5): 418-24 (1995).

Greenwald, et al., *Tetracyclines Suppress Matrix Metalloproteinase Activity in Adjuvant Arthritis and in Combination with Flurbiprofen, Ameliorate Bone Damage*, Journal of Rheumatology 19(6): 927-38 (1992).

Griscelli, et al., *Angiostatin gene transfer: Inhibition of tumor growth in vivo by blockage of endothelial cell proliferation associated with a mitosis arrest*, Proceedings of the National Academy of Sciences U.S.A., 95(11): 6367-72 (1998).

Hanessian, et al., *Picking The $S_1$ $S_1$ and $S_2$ Pockets of Matrix Metalloproteinases, A Niche for Potent Acyclic Sulfonamide Inhibitors*, Biooroganic Medical Chemistry Letters 9(12): 1691-96 (1999).

Hanglow, et al., *Peptides based on the conserved prodomain sequence of matrix metalloproteinases inhibit human stromelysin and collagenase*, Agents Actions 39 Spec. No.: C148-50 (1993).

Investigative Opthalmology Visual Science, vol. 41, No. 4, S640 (2000).

Jacobson, et al., *Structure-Based Design and Synthesis of a Series of Hydroxamic Acids With a Quaternary-Hydroxy Group in Pl As Inhibitors of Matrix Metalloproteinases*, Biooroganic Medical Chemistry Letters 8(7): 837-42 (1998).

Kawakami, et al., XP 002201344—AN 1999—2290406. "*Corneal neovascularization inhibitor useful e.g. with corneal grafts,*" Abstract WO 9913909 (1999).

Kishnani, et al., *Identification and Characterization of Human Tissue Inhibitor of Metalloproteinase-3 and Detection of Three Additional Metalloproteinse Inhibitor Activities in Extracellular Matrix*, Matrix Biology 14(6): 479-88 (1995).

Klement, et al., *Continuous low-dose therapy with vinblastine and VEGF receptor-2 antiboyd induces sustained tumor regression without overt toxicity*, J. Clin. Invest. 105(8): R15-24 (2000).

Klein, et al., *The Wisconsin Epidemiologic Study of Diabetic Retinopathy*, Arch. Ophth. 112: 1217-1228 (1994).

Lyons-Giordano, et al., *The Effect of Heparin on Fibronectin and Thrombospondin Synthesis and mRNA Levels in Cultured Human Endothelial Cells*, Exp. Cell Research 186(1): 39-46 (1990).

Melchiori, et al., *Inhibition of Tumor Cell Invasion of a Highly Conserved Peptide Sequence from the Matrix Metalloproteinase Enzyme Prosegment*,Cancer Research 52(8): 2353-56 (1992).

Murphy, A.N., et al., *Tissue Inhibitor of Metalloproteinases-2 Inhibits bFGF-Induced Human Microvascular Endothelial Cell Proliferation*, Journal of Cell Physiology 157(2): 351-58 (1993).

Murphy, G., et al., *The N-Terminal Domain of Tissue Inhibitor of Metalloproteinases Retains Metalloproteinase Inhibitory Activity*, Biochemistry 30(33): 8097-102 (1991).

Odake, et al., *Inhibition of Matrix Metalloproteinases By Peptidyl Hydroxamic Acids*, Biochem Biophys Res Commun 199(3): 1442-46 (1994).

Ostendorf, et al., *VEGF $_{165}$ mediates glomerular endothelial repair*.

Pikul, et al., *Design and Synthesis of Phosphinamide-Based Hydroxamic Acids as Inhibitors of Matrix Metalloproteinases*, Journal of Medical Chemistry 42(1): 87-94 (1999).

Possati, et al., *Antiangiogenic, antitumoural and antimetastatic effects of two distamycin A derivatives with anti-HIV-1 Tat activity in Kaposi's sarcoma-like murine model*, Clin. Exp. Metastatis 17(7): 575-82 (1999).

Shapiro, et al., *Dexamethasone Selectively Modulates Basal and Lipopolysaccharide-Induced Metalloproteinase and Tissue Inhibitor of Metalloproteinase Production By Human Alveolar Macrophages*, Journal of Immunology 146(8): 2724-29.

Siemeister, et al., An antagonistic vascular endothelial growth factor (VEGF): variant inhibits VEGF-stimulated receptor autophosphorylation and proliferation of human endothelial cells, Proceedings of the National Academy of Sciences U.S.A. 95: 4625-29 (1998).

Stack, et al., *Application of N-Carboxyallkyl Peptides to the Inhibition and Affinity Purification of the Porcine Matrix Mettoproteniases Collagenase, Gelatinase, and Stromelysin*, Arch. Biochem. Biophys. 287(2): 240-49 (1991).

Steinman, et al., *The Design, Synthesis, and Structure-Activity Relationships of a Series of Macrocyclic MMP Inhibitors*, Bioorganic Medical Chemistry Letters 8(16): 21087-92 (1998).

Sunamura, et al., *The Antiangiogenesis Effect of Interleukin 12 During Early Growth of Human Pancreatic Cancer in SCID Mice.* Pancreas 20(3): 227-33 (2000).

Wallon, et al., *Polyamine-Dependent Expression of the Matrix Mettaloproteinase Matrilysin in a Human Colon Cancer-Derived Cell Line*, Mol. Carcinog, 11(3): 138-44 (1994).

Wentworth, et al., Effect of a Metalloproteinase Inhibitor on Established Corneal Ulcers After an Alkali Burn, Invest. Ophthalmol. Vis. Sci. 33(7): 2174-79 (1992).

Willis, et al., *Liposome-Anchored Vascular Endothelial Growth Factor Aptamers*, Bioconjug. Chem. 9(5): 573-82 (1998).

Zhang, et al., *Structural interaction of natural and synthetic inhibitors with the venom metalloproteinase, atrolysin C (form d)*, Proceedings of the National Academy of Sciences U.S.A. 91: 8447-51 (1994).

Dayle H. Geroski and Henry F. Edlehauser, *Drug Delivery for Posterior Segment EyeDisease*, ARVO 41(5) 961-4 (2000).

Raza et al., "Matrix Metalloproteinases: Pro- and Anti-Angiogenic Activities", *J Investig Dermatol Symp Proc*, 5(1):47-54 (2000) (abstract only).

Stack et al., "Application of N-Carboxyalkyl Peptides to Inhibition and Affinity Purification of the Porcine Matrix Metalloproteinases Collagenase, Gelatinase, and Stromelysin", *Arch Biochem Biophys*, 297(2):393 (1992) (abstract only).

\* cited by examiner

METHODS AND COMPOSITIONS FOR TREATING AND INHIBITING RETINAL NEOVASCULARIZATION

FIELD OF THE INVENTION

This invention relates to retinal neovascularization, and more particularly to the prophylactic and therapeutic treatment of retinal disorders associated with neovascularization using topical ophthalmic compositions.

BACKGROUND OF THE INVENTION

Retinal neovascularization is a condition in which new blood vessels grow and proliferate in the retina, typically in response to a decrease in blood flow to the retina. Neovascularization typically improves the flow of blood in a tissue by creating new blood vessels instead of replacing the existing vasculature. The retina possesses a complex architecture of capillaries that supports many different neuronal and photoreceptor cells without interfering with the images that pass through the lens and are processed on the retina's surface. The formation of new blood vessels may destroy this complex architecture and detract from normal functioning of the eye by presenting abnormal conditions such as bleeding, which may cause hazy vision or even total vision loss, and scarring, which may result in retinal dislocation or invasion of the retina from underlying tissue. Neovascularization may progress slowly, resulting generally in the formation of new vessels and fibrous tissue, or rapidly, in which case widespread capillary closure, soft exudate formation, hemorrhages, and blindness are typical.

Neovascular diseases of the retina include diabetic retinopathy, age-related macular degeneration, neovascular glaucoma, retinopathy of prematurity, sickle-cell retinopathy, retinal vein occlusion, oxygen induced retinopathy, and neovascularization due to ocular insults such as traumatic or surgical injury, or transplantation of eye tissue. Other conditions or diseases associated with the manifestation of retinal neovasularization include any disease or condition where a part of the retina is subject to a relatively non-perfused state compared to surrounding tissue, where any one or more of the proteins, proteinases, hormones, or cellular signals associated with angiogenesis are detected, or where new vessel growth can be detected or observed. In addition, diseases implicating matrix metalloproteinase activity, endothelial invasion, or the generation of new blood vessels may also be associated with retinal neovascularization according to this invention.

Neovascularization involves both the degradation of tissue through enzymatic action and the formation of new tissue. A crucial event in the retinal neovascularization process is the migration of epithelial cells, which involves proteolysis of basement membrane components, typically by one or more proteinases. At active neovascularization sites, both the high (54 kD) and low (33 kD) molecular weight forms of the protein urokinase have been found at levels significantly higher than in normal retinas. The levels of both pro and active forms of the matrix metalloproteinases (MMP) MMP-2 (gelatinase) and MMP-9 are also significantly elevated in neovascular membranes in comparison to normal retinas. (See Das et al., Investigative Ophthalmology & Visual Sciences 40:809–13 (1999); Coors et al., Investigative Ophthalmology & Visual Sciences 40(4):S231 (1999)). Typically the active forms of MMPs such as collagenase, stromelysin and gelatinase are not present at detectable levels in normal retinas.

Diabetic retinopathy is the leading cause of blindness among working age adults in the United States. Initially, the high blood glucose levels common to persons with diabetes mellitus cause an increase in growth factor levels in the eyes. This condition is known as the "pre-diabetic retinopathy stage" and can lead to retinopathy if not prophylactically treated. Non-proliferative or early-stage diabetic retinopathy, also known as "background diabetic retinopathy," is characterized by thickening of the basement membrane, loss of retinal pericytes, microvascular abnormalities, intraretinal microaneurysms, retinal hemorrhages (known as "dot blot" or "cotton wool" spots), retinal edema, capillary closure, and soft and hard exudates. Late-stage or proliferative diabetic retinopathy, which is characterized by neovascularization and fibrovascular growth, i.e., scarring involving glial and fibrous elements, from the retina or optic nerve over the inner surface of the retina or into the vitreous cavity. Retinal detachment may also occur.

Age-related macular degeneration is one of the leading causes of blindness in older adults in the United States, and may account for up to 30 percent of all bilateral blindness among Caucasian Americans. This disease is characterized by loss of central vision, usually in both eyes, due to damage to the retinal pigment epithelial (RPE) cells. RPE cells are aligned in the lowest layer of the retina, on the Bruch's membrane, and absorb the light which reaches the retina so as to prevent reflection. RPE cells also constitute the blood-retinal barrier which partitions the visual cells and the vascular layer of choroid together with the Bruch's membrane. In general, RPE cells have important physical and physiological functions, such as sustainment and regeneration of visual cells.

Retinopathy of prematurity (ROP) is a common cause of blindness in children in the United States. Premature infants are exposed to hyperoxic conditions after birth even without the administration of supplemental oxygen due to the higher partial pressure of oxygen in the atmosphere as compared to in utero conditions. This relative hyperoxia is necessary for the survival of premature infants yet may result in ROP. The hyperoxic atmosphere causes retinal blood vessels to stop developing into the peripheral retina, resulting in ischemia and localized hypoxic conditions as the metabolic demands of the developing retina increase. The resulting localized hypoxia stimulates retinal neovascularization. The neovascularization usually regresses, but may lead to irreversible vision loss. There are at least 10,000 new cases per year of ROP with a worldwide estimate of 10 million total cases.

Known treatments for retinal neovascularization include panretinal laser coagulation, cryotherapy, laser therapy, and chemotherapy. Panretinal laser coagulation is the classic treatment for proliferative diabetic retinopathy, but may have serious side effects such as foveal burns, hemorrhaging, retinal detachment, choroidal vessel growth, decreased peripheral and night vision, and changes in color perception. Cryotherapy and laser therapy may be used to treat ROP and other neovascular diseases, but are not completely effective and may damage the eye and result in decreased vision. In some diseases such as exudative cases of age-related macular degeneration, temporary prevention of vision loss may be achieved by laser therapy, but no permanent treatment is available for some forms of diseases associated with retinal neovascularization.

Chemotherapy has advantages compared to photocoagulation and cryotherapy in that the tissue invasion is smaller and the stress placed on the ocular tissue is lower. The number of effective drugs, however, is quite small. Compounds which inhibit the action of MMPs involved in connective tissue breakdown are of potential value in the treatment of angiogenesis-dependent diseases such as proliferative retinopathies, neovascular glaucoma, and other forms of retinal neovascularization. Certain agents have been proposed for inhibiting MMPs (see U.S. Pat. No. 5,917,090). In particular, MMP inhibitors have been employed as potential treatments to the retina via intraorbital administration, tissue specific microinjection, or intravitreal injection (see, e.g., European Patent Publication EP 0930067, published Jul. 21, 1999; U.S. Pat. No. 5,260,059; and published PCT Application WO 97/18835). While these treatments may act directly at the retina, they have the disadvantage of being difficult to administer and of requiring the co-administration of anesthetic to the patient.

Topical treatment would be preferred because a topical composition may be self-administered by a patient, and does not require the co-administration of anesthetics. Topical compositions are generally ineffective at delivering a therapeutically effective amount of an active ingredient to the retina, however, due to a lack of permeation through the conjunctiva and sclera, and the presence of the blood-retinal barrier. Some ophthalmic treatment agents, such as the highly soluble β-blocking agents, have been found to reach the retina after topical administration because they are absorbed into the blood stream and passed systemically to the retina (see Osborne et al., Exp. Eye Res. 69:331–42). This method is ineffective for relatively insoluble agents, such as MMP inhibitors, that do not pass through the blood-retinal barrier.

What is needed is a topical ophthalmic composition for the prophylactic and therapeutic treatment of retinal neovascularization that is capable of delivering a therapeutically effective amount of an active ingredient to the retina. Also needed are methods for prophylactic and therapeutic treatments of retinal neovascularization.

SUMMARY OF THE INVENTION

The present invention relates to the unexpected discovery that topical administration of the compositions of the present invention, which comprise a batimastat compound, are capable of delivering a therapeutically effective amount of a batimastat compound to the retina. This discovery was unexpected because prior methods of topical administration of relatively insoluble compounds failed to result in therapeutically effective amounts of the compound reaching the retinal tissue and being retained therein.

The present invention provides methods for treating retinal neovascularization in a mammal in need of such treatment, or preventing retinal neovascularization in a mammal susceptible to developing retinal neovascularization, comprising topically administering to the eye a composition capable of delivering a therapeutically effective amount of a batimastat compound to the retina. Methods for treating retinal neovascularization in a mammal in need of such treatment, or preventing retinal neovascularization in a mammal susceptible to developing retinal neovascularization, comprising administering topically to the eye a composition comprising a batimastat compound, and delivering to the retina a therapeutically effective amount of the batimastat compound, are also provided.

Other methods of the present invention include methods for treating retinal neovascularization in a mammal in need of such treatment, or preventing retinal neovascularization in a mammal susceptible to developing retinal neovascularization, comprising a batimastat compound and a polymeric suspension agent, where the composition is capable of delivering to the retina a therapeutically effective amount of the batimastat compound.

Further provided are methods for treating retinal neovascularization in a mammal in need of such treatment, or preventing retinal neovascularization in a mammal susceptible to developing retinal neovascularization, comprising topically administering to the eye a composition capable of delivering a therapeutically effective amount of a batimastat compound to the retina, where the composition comprises a polymeric suspension agent and about 0.01 to about 3 percent, by weight, of the batimastat compound.

The present invention also provides ophthalmic compositions for use in treating or preventing retinal neovascularization in a mammal by topical administration to the eye, comprising a therapeutically effective amount of a batimastat compound, and ophthalmic compositions for use in treating or preventing retinal neovascularization in a mammal by topical administration to the eye, comprising a therapeutically effective amount of a batimastat compound, and a polymeric suspension agent.

Also provided are topical ophthalmic compositions for use in treating or preventing retinal neovascularization in a mammal, comprising a batimastat compound and a polymeric suspension agent, where the composition is capable of delivering a therapeutically effective amount of the batimastat compound to the retina. Further provided are topical ophthalmic compositions for use in treating or preventing retinal neovascularization in a mammal, comprising about 0.1 to about 0.3 percent by weight of batimastat and about 0.5 to about 1.25 percent by weight of a polymeric suspension agent, where the composition is capable of delivering a therapeutically effective amount of batimastat to the retina, and topical ophthalmic compositions for use in treating or preventing retinal neovascularization in a human, comprising about 0.1 to about 0.3 percent by weight of batimastat and about 0.5 to about 1.5 percent by weight of a polycarbophil, where the composition is capable of delivering a therapeutically effective amount of batimastat to the retina.

The polymeric suspension agents used in the methods and compositions of the present invention may comprise one or more polymers. In particular, cross-linked polymers, acrylic acid-containing polymers and carboxyl-vinyl-containing polymers may be used. Particularly preferred polymers include polycarbophil, the DuraSite® polymeric delivery system (InSite Vision, Inc., Alameda, Calif.), and mucomimetic polymers (see, e.g., U.S. Pat. No. 5,932,572).

Additional advantages and features of the present invention will be apparent from the following detailed description, drawings and examples which illustrate preferred embodiments of the invention.

DETAILED DESCRIPTION OF PREFERRED EMBODIMENTS

Figure 1:
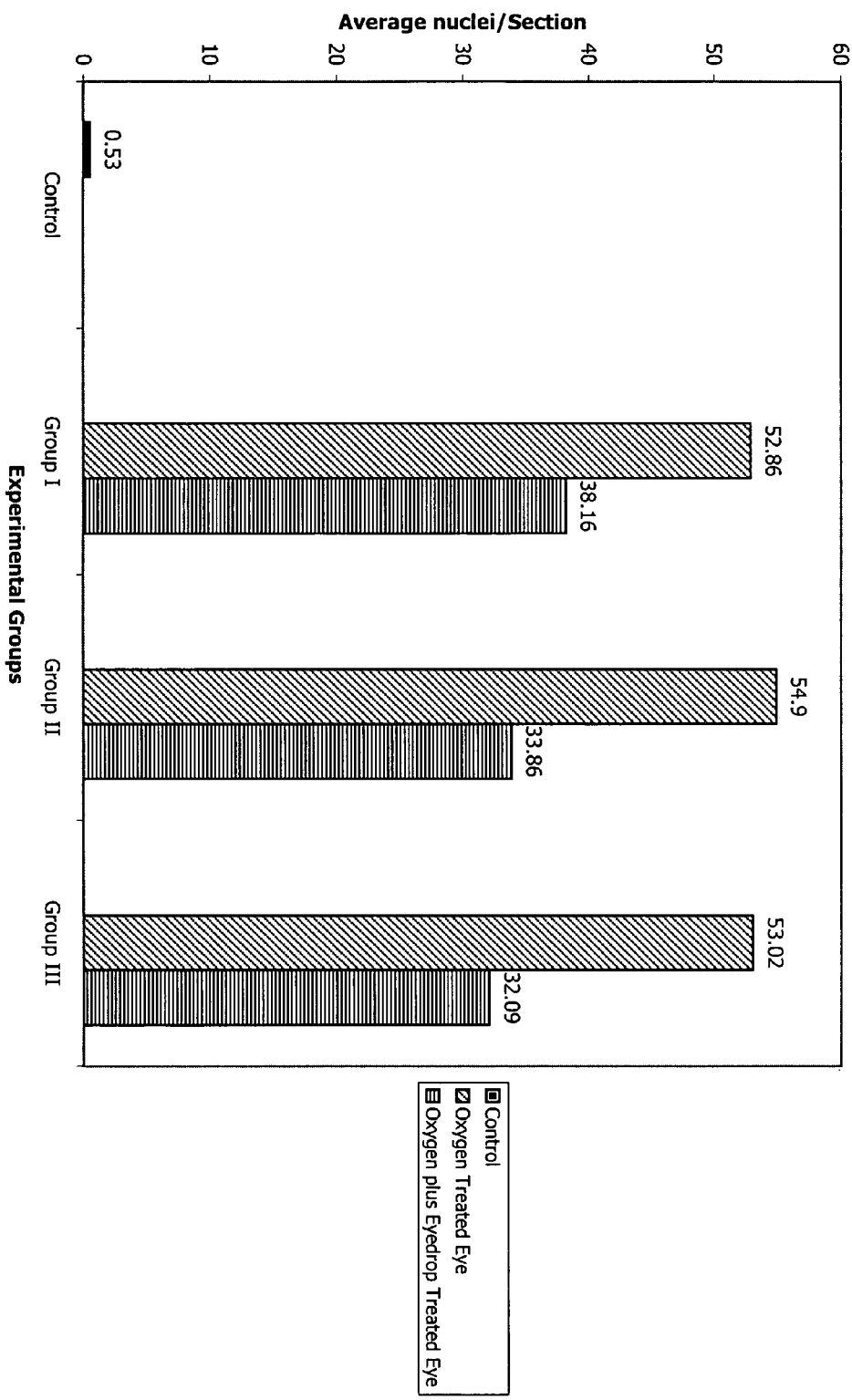
FIG. 1 depicts the effects of an MMP inhibitor on the number of neovascularization events in a section of murine retinal tissue.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

One skilled in the art may refer to general reference texts for detailed descriptions of known techniques discussed herein or equivalent techniques. These texts include Current Protocols in Molecular Biology (Ausubel et al., eds., John Wiley & Sons, N.Y., and supplements through June 1999), Current Protocols in Immunology (Coligan et al., eds., John Wiley & Sons, N.Y., and supplements through June 1999), and Current Protocols in Pharmacology (Enna et al., eds., John Wiley & Sons, N.Y., and supplements through June 1999), Fingl et al., The Pharmacological Basis of Therapeutics (1975), and Remington's Pharmaceutical Sciences (Mack Publishing Co., Easton, Pa., 18$^{th}$ edition (1990)), for example. These texts may also be referred to in making or using an aspect of the present invention.

The present invention concerns methods and compositions for the prophylactic and therapeutic treatment of retinal neovascularization and related diseases with a batimastat compound. The compositions and the methods employing them have been found to unexpectedly deliver therapeutically effective amounts of the relatively insoluble MMP inhibitor batimastat to the retina when administered topically to the eye of an animal. A batimastat compound refers to any pharmaceutically acceptable salt, derivative, stereoisomer, or mixture of stereoisomers of batimastat, or to batimastat itself. Batimastat, also known as BB-94, is a relatively insoluble chemical having the chemical name [2-R-[1(S*),2R*,3S*]]-N$^4$-hydroxy-N$^1$-[2-(methylamino)-2-oxo-1-(phenylmethyl)ethyl]-2-(2-methylpropyl)-3-[(2-thienylthio)methyl]butanediamide or (2S,-3R)-5-methyl-3-[[(αS)-α-(methylcarbamoyl)phenethyl]carbamoyl]-2-[(2-thienylthio)methyl]hexanohydroxamic acid, and the formula:

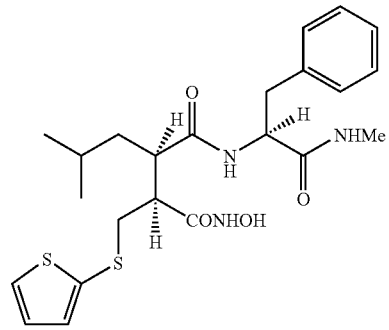

Batimastat may be prepared in a number of ways and occur in a number of different states of stereoisomeric purity. One skilled in the art is familiar with techniques for preparing the compound itself (see, e.g., U.S. Pat. No. 5,872,152 and the references cited therein). Pharmaceutically acceptable salts or derivatives of batimastat may also be used in the methods and compositions of the present invention. The term "pharmaceutically acceptable salt" used herein refers to those salts of the parent compound that do not significantly or adversely affect the pharmaceutical properties (e.g., toxicity, efficacy, etc.) of the parent compound. Pharmaceutically acceptable salts administrable by means of the compositions of this invention include, for example, chloride, iodide, bromide, hydrochloride, acetate, nitrate, stearate, palmoate, phosphate, and sulfate salts. Exemplary techniques for producing pharmaceutically acceptable derivatives of batimastat include methylation, halogenation, acetylation, esterification, and hydroxylation. Other examples also include those selected or derived from those described in U.S. Pat. No. 5,917,090.

The present invention also concerns methods and compositions for the prophylactic and therapeutic treatment of retinal neovascularization and related diseases with other MMP inhibitors, which include the hydroxamic acid-based compounds described in U.S. Pat. No. 5,240,958, which includes compounds of the general formula:

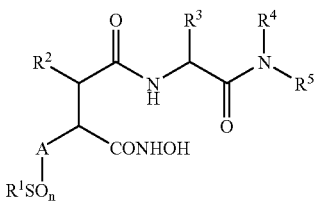

wherein:

$R^1$ represents a hydrogen atom, $C_1$–$C_6$ alkyl, phenyl, thienyl, substituted phenyl, phenyl($C_1$–$C_6$)alkyl, heterocyclyl, ($C_1$–$C_6$)alkylcarbonyl, phenacyl or substituted phenacyl group; or, when N=O, R¹ represents SR^x, wherein R^x represents a group:

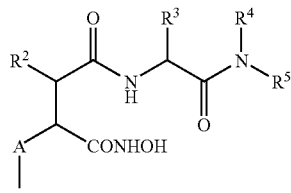

R¹ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl or cycloalkenyl($C_1$–$C_6$)alkyl group;
R³ represents an amino acid side chain or a $C_1$–$C_6$ alkyl, benzyl, ($C_1$–$C_6$ alkoxy) benzyl, benzyloxy($C_1$–$C_6$) or benzyloxybenzyl group;
R⁴ represents a hydrogen atom or a $C_1$–$C_6$ alkyl group;
R⁵ represents a hydrogen atom or a methyl group;
n is an integer having the value 0, 1 or 2; and
A represents a $C_1$–$C_6$ hydrocarbon chain, optionally substituted with one or more $C_1$–$C_6$ alkyl, phenyl or substituted phenyl groups;

or a salt thereof.

As used herein the term "$C_1$–$C_6$ alkyl" refers to a straight or branched chain alkyl moiety having from one to six carbon atoms, including for example, methyl, ethyl, propyl, isopropyl, butyl, t-butyl, pentyl and hexyl, and cognate terms (such as "$C_1$–$C_6$ alkoxy") are to be construed accordingly.

The term "$C_1$–$C_6$ alkenyl" refers to a straight or branched chain alkyl moiety having one to six carbons and having in addition one double bond, of either E or Z stereochemistry where applicable. This term would include, for example, an alpha, beta-unsaturated methylene group, vinyl, 1-propenyl, 1- and 2-butenyl and 2-methyl-2-propenyl.

The term "cycloalkyl" refers to a saturated alicyclic moiety having from 3 to 8 carbon atoms and includes for example, cyclopropyl, cyclobutyl, cyclopentyl and cyclohexyl.

The term "cycloalkenyl" refers to an unsaturated alicycle having from 3 to 8 carbon atoms and includes cyclopropenyl, cyclobutenyl and cyclopentenyl, cyclohexenyl.

The term "substituted", as applied to a phenyl or other aromatic ring, means substituted with up to four substituents each of which independently may be $C_1$–$C_6$ alkyl, $C_1$–$C_6$ alkoxy, hydroxy, thiol, $C_1$–$C_6$ alkylthiol, amino, halo (including fluoro, chloro, bromo and iodo), trifluoromethyl or nitro.

The term "amino acid side chain" means a characteristic side chain attached to the —CH(NH₂)(COOH) moiety in the following R or S amino acids: glycine, alanine, valine, leucine, isoleucine, phenylanine, tyrosine, tryptophan, serine, threonine, cysteine, methionine, asparagine, glutamine, lysine, histidine, arginine, glutamic acid and aspartic acid.

The term "hydrocarbon chain" includes alkylene, alkenylene and alkynylene chains of from 1 to 6 carbon atoms. Preferably the carbon atom of the hydrocarbon chain nearest to the hydroxamic acid group is a methylene carbon atom.

There are several chiral centres in the compounds according to the invention because of the presence of asymmetric carbon atoms. The presence of several assymmetreic carbon aroms gives rise to a number of diastereomers with the appropriate R or S stereochemistry at each chiral centre. General formula I and, where appropriate, all other formulae in this specification are to be understood to include all such stereoisomers and mixtures (for example racemic mixtures) thereof. Compounds in which the chiral centre adjacent the substituent R³ has S stereochemistry and/or the chiral centre adjacent the substituent R² has R stereochemistry are preferred.

Particularly preferred neovascular inhibitory agents are those having the general formula:

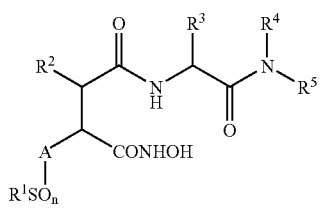

where R¹ represents thienyl; R² represents a hydrogen atom or a $C_1$–$C_6$ alkyl, $C_1$–$C_6$ alkenyl, phenyl($C_1$–$C_6$) alkyl, cycloalkyl($C_1$–$C_6$)alkyl or cycloalkenyl($C_1$–$C_6$)alkyl group; R³ represents an amino acid side chain or a $C_1$–$C_6$ alkyl, benzyl, ($C_1$–$C_6$alkoxyl)benzyl or benzyloxy($C_1$–$C_6$alkyl) or benzyloxy benzyl group R⁴ represents a hydrogen atom or a $C_1$–$C_6$ alkyl group; R⁵ represents a hydrogen atom or a methyl group; n is an integer having the value 0, 1, or 2; and A represents a $C_1$–$C_6$ hydrocarbon chain, optionally substituted with one or more $C_1$–$C_6$ alkyl, phenyl or substituted phenyl groups; or a salt thereof.

In addition, the compositions of the invention may be enriched with one or more of the stereoisomers of batimastat, or may be substantially optically pure with respect to one stereoisomer. The methods for using batimastat may also comprise enriched stereoisomers or mixtures. One skilled in the art is familiar with designing synthetic schemes that employ one or more optically pure reagents or intermediates, or stereoisomerically enriched reagents or intermediates, resulting in either a substantially optically pure composition or a stereoisomerically enriched composition. A substantially optically pure composition contains about 85 to about 95 percent, or higher, of one stereoisomer. Chromatographic, enzymatic, or selective crystallization techniques for enriching or purifying stereoisomers of batimastat, mixtures of batimastat compounds, or any intermediate or reagent used to prepare a batimastat compound may also be used.

In a preferred embodiment, the compositions of the present invention comprise a therapeutically effective amount of a batimastat compound. Preferred concentrations of batimastat compound(s) in the compositions of the present invention are in the range of about 0.01 to about 3 percent (wt/wt). A more preferred range of concentrations is from about 0.05 to about 0.5 percent, and even more preferred concentrations are from about 0.1 to about 0.3 percent.

As used herein, the term "therapeutically effective amount" means the total amount of each active component of the pharmaceutical composition or method that is sufficient to show a meaningful patient benefit, i.e., healing of chronic conditions characterized by neovascularization, a reduction in neovascularization itself, an increase in rate of healing of such conditions, or a detectable change in the levels of MMP or other related proteinases in the retina or surrounding tissue. When applied to an individual active ingredient, administered alone, the term refers to that ingredient alone. When applied to a combination, the term refers to combined amounts of the active ingredients that result in the therapeutic effect, whether administered in combination, serially, or simultaneously.

Therapeutic efficacy and toxicity of the compositions may be determined by standard pharmaceutical, pharmacological, and toxicological procedures in cell cultures or experimental animals. For example, numerous methods of determining $ED_{50}$ (the dose therapeutically effective in 50 percent of the population) and $LD_{50}$ (the dose lethal of 50 percent of the population) exist. The dose ratio between therapeutic and toxic effects is the therapeutic index, and it can be expressed as the ratio $ED_{50}/LD_{50}$. Compositions exhibiting high therapeutic indices are preferred. The data obtained from cell culture assays or animal studies may be used in formulating a range of dosages for human use. The dosage is preferably within a range of concentrations that includes the $ED_{50}$ with little or no toxicity, and may vary within this range depending on the dosage form employed, sensitivity of the patient, and the route of administration.

The pH of the inventive compositions is preferably between about 6 and about 8, and may be adjusted for the particular batimastat compound(s) used. Purified water USP and various acids and bases suitable for ophthalmic use, or combinations of acids and bases, may be used for adjusting the pH of the compositions. Non-limiting examples of acids and bases include acetic acid, boric acid, citric acid, lactic acid, phosphoric acid, hydrochloric acid, sodium hydroxide, sodium phosphate, sodium borate, sodium citrate, sodium acetate, sodium lactate, and TRIS.

The osmotic pressure of the compositions may be adjusted by methods known in the art to be between about 40 to about 400 milliosmolar (mOsM), more preferably between about 100 to about 300 mOsM. A preferred method of adjusting osmotic pressure is the addition of physiologically and ophthalmically acceptable salts. Sodium chloride, which approximates physiological fluid, is the preferred salt, for use in concentrations ranging from about 0.01 to about 1 percent by weight, or any value in that range. Preferably, the concentration is between about 0.1 to about 1 percent. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like, can also be used in addition to or instead of sodium chloride to achieve osmotic pressures within the above-stated ranges.

Additional components of the composition may be chosen from any of those used in or capable of being used in a pharmaceutical formulation, especially those designed for topical administration to the eye. A non-exclusive list of components includes preservatives, stabilizers, chelating agents, dyes, antibiotics, antimicrobials, and anti-fungal agents. Preservatives such as benzalkonium chloride may be used in a range between about 0.001 to 1 percent by weight, or any value in this range. The compositions of the present invention may further comprise pharmaceutically acceptable carriers, excipients, gels, solutions, or diluents suitable for topical ophthalmic administration, and may include pharmaceutically acceptable polymeric suspension agents. Suitable carriers or excipients include, but are not limited to, calcium carbonate, calcium phosphate, various sugars, starches, cellulose derivatives, gelatin, and polymers such as polyethylene glycol. Suitable techniques for the formulation and administration of the compositions of the present invention may be found in Remington's Pharmaceutical Sciences, $18^{th}$ edition (1990).

In another preferred embodiment, the compositions of the present invention comprise a therapeutically effective amount of a batimastat compound and a pharmaceutically acceptable polymeric suspension agent. Exemplary polymeric suspension agents include dextrans, polyethylene glycols, polyvinylpyrrolidone, polysaccharide gels, Gelrite®, cellulosic polymers like hydroxypropyl methylcellulose, and carboxyl-containing polymers such as polymers or copolymers of acrylic acid, as well as other polymeric demulcents. A preferred polymeric suspending agent is a water-swellable, water-insoluble polymer, especially a crosslinked carboxyl-containing polymer.

Crosslinked carboxyl-containing polymers that can be used in practicing this invention are, in general, well known in the art. In a preferred embodiment, these polymers may be prepared from at least about 90 percent, and preferably from about 95 to about 99.9 percent by weight, based on the total weight of monomers present, of one or more carboxyl-containing monoethylenically unsaturated monomers. Acrylic acid is the preferred carboxyl-containing monoethylenically unsaturated monomer, but other unsaturated, polymerizable carboxyl-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like may be used in addition to or instead of acrylic acid.

The polymers may be crosslinked by a polyfunctional crosslinking agent, preferably a difunctional crosslinking agent. The amount of crosslinking should be sufficient to form insoluble polymer particles, but not so great as to unduly interfere with sustained release of the batimastat compound. Typically the polymers are only lightly crosslinked. Preferably the crosslinking agent is contained in an amount of from about 0.01 to about 5 percent, preferably from about 0.1 to about 5.0 percent, and more preferably from about 0.2 to about 1 percent, based on the total weight of monomers present.

Suitable crosslinking agents include non-polyalkenyl polyether difunctional crosslinking monomers, such as divinyl glycol; 2,3-dihydroxyhexa-1,5-diene; 2,5-dimethyl-1,5-hexadiene; divinylbenzene; N,N-diallylacrylamide; N,N-diallylmethacrylamide, and the like. Other suitable crosslinking agents include polyalkenyl polyether crosslinking agents such as polyallyl sucrose or polyallyl pentaerythritol (see, e.g., U.S. Pat. No. 2,798,053), and diolefinic non-hydrophilic macromeric crosslinking agents as disclosed in U.S. Pat. Nos. 4,192,827 and 4,136,250.

The crosslinked carboxyl-vinyl polymers may be made from a carboxyl-vinyl monomer or monomers as the sole monoethylenically unsaturated monomer present, together with a crosslinking agent or agents. Preferably, the polymers are ones in which up to about 40 percent, and preferably from about 0 to about 20 percent by weight, of the carboxyl-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, as well as the monoethylenically unsaturated monomers disclosed in U.S. Pat. No. 4,548,990.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, the polycarbophil-containing DuraSite® polymeric delivery system (InSite Vision, Inc., Alameda, Calif.), which is a sustained release topical ophthalmic delivery system that releases a drug at a controlled rate, is used as the polymeric suspension agent in the compositions of the present invention.

The crosslinked carboxyl-vinyl polymers used in practicing this invention are preferably prepared by suspension or emulsion polymerizing the monomers, using conventional free radical polymerization catalysts, to a dry particle size of not more than about 1 to 10 μm in equivalent spherical diameter; e.g., to provide dry polymer particles ranging in size from about 1 to about 30 μm, and preferably from about 5 to about 20 μm, in equivalent spherical diameter. Using polymer particles that were obtained by mechanically milling larger polymer particles to this size is preferably avoided. In general, such polymers will have a molecular weight that has been variously reported as being from about 250,000 to about 5,000,000,000.

In the most preferred embodiment of the invention, the particles of crosslinked carboxyl-vinyl polymer are monodisperse, meaning that they have a particle size distribution such that at least 80 percent of the particles fall within a 10 μm band of major particle size distribution. More preferably, at least 90 percent and most preferably at least 95 percent, of the particles fall within a 10 μm band of major particle size distribution. Also, a monodisperse particle size means that there is no more than 20 percent, preferably no more than 10 percent, and most preferably no more than 5 percent particles of a size below 1 μm. The use of a monodispersion of particles will give maximum viscosity and an increased eye residence time of the ophthalmic medicament delivery system for a given particle size. Monodisperse particles having a particle size of 30 μm and below are most preferred. Good particle packing is aided by a narrow particle size distribution.

The compositions of the present invention normally contain 0.01 to 3 percent, preferably 0.05 to 0.5 percent, more preferably 0.1 to 0.3 percent, of the batimastat compound, and 0.1 to 10 percent, preferably 0.5 to 6.5 percent, of a polymeric suspension agent. In the case of the above described water-insoluble, water-swellable crosslinked carboxyl-vinyl polymer, a more preferred amount of the polymeric suspending agent is an amount ranging from about 0.5 to about 2.0 percent, or any chosen range between these percentages. Especially preferred embodiments comprise from about 0.5 percent to about 1.3 percent polymer, and in certain embodiments from about 0.6 to about 0.9 percent, based on the weight of the composition. Although referred to in the singular, it should be understood that one or more species of polymeric suspension agent, such as the crosslinked carboxyl-containing polymer, may be used with the total amount falling within the stated ranges. In one preferred embodiment, the composition contains from about 0.5 to about 2.0 percent, or any chosen range between these percentages, of a polycarbophil, such as NOVEON AA-1, and even more preferred is from about 0.75 to about 1.3 percent.

In one embodiment, the amount of insoluble lightly crosslinked carboxyl-vinyl polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. Alternatively, when the viscosity is within the range of 500 to 3000 centipoise, it may be determined by a Brookfield Model DV-11+, choosing a number cp-52 spindle at 6 rpm. One skilled in the art is familiar with methods for adjusting and optimizing viscosity ranges for pharmaceutical compositions. When water soluble polymers such as hydroxypropyl methylcellulose (HPMC) are used as suspension agents, the viscosity will typically be about 10 to about 400 centipoise, more typically about 10 to about 200 centipoises or about 10 to about 25 centipoise.

Also provided are methods for prophylactic and therapeutic treatment of diseases and conditions manifesting or associated with retinal neovascularization comprising administering a topical ophthalmic composition of the present invention to an animal in need of such treatment. Another method provided is a method for identifying or selecting a topical ophthalmic composition for administering a batimastat compound. The method comprises selecting a batimastat compound, selecting a polymer-type carrier or polymeric suspension agent, and detecting the inhibition of proteinase activity in the retina.

The duration of prophylactic and therapeutic treatment will vary depending on the particular disease or condition being treated. Some diseases lend themselves to acute treatment whereas others require long-term therapy. Proliferative retinopathy can reach a threshold in a matter of days as seen in ROP, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also remain in the proliferative phase for a longer period of time. Diabetic retinopathy will eventually become quiescent as the vasoproliferative signal diminishes due to neovascularization and destruction of the retina.

Application of the teachings of the present invention to a specific problem or environment is within the capabilities of one having ordinary skill in the art in light of the teachings contained herein. Examples of the products and processes of the present invention appear in the following examples.

EXAMPLE 1

Preparation of Compositions Containing a Batimastat Compound

Various formulations of the compositions of the present invention were compounded, and are listed in the following table.

| Compound | Formulation 1 (w/w %) | Formulation 2 (w/w %) | Formulation 3 (w/w %) |
| --- | --- | --- | --- |
| HPMC | 2.5 | | |
| Batimastat | 0.3 | 0.3 | 0.3 |
| Mannitol | | | 1.0 |
| Sorbitol | 1.5 | | |
| Glycerin | 1.0 | | |
| Poloxamer 407 | 0.5 | 0.05 | 0.05 |
| Polycarbophil | | 1.25 | 0.85 |
| NaCl | | 0.6 | 0.2 |
| Sodium Citrate Dihydrate | | 0.35 | 0.35 |
| Benzalkonium Chloride (BAK) | | | 0.008 |
| EDTA | | 0.1 | 0.1 |
| Water | q.s. to 100% | q.s. to 100% | q.s. to 100% |
| NaOH | q.s. to pH 6 | q.s. to pH 6 | q.s. to pH 6 |

The physical and chemical characteristics of the compositions of the invention may be modified or optimized according to the skill in the art. Thus, pH, osmotic pressure, viscosity, and the content of various additional components may be chosen from any appropriate range known or modified from the examples given here. The methods for preparing and selecting exemplary formulations containing polymeric suspension agents are described in U.S. Pat. Nos. 5,188,826 and 5,192,535, for example. In general, the pharmaceutical compositions of the invention may be manufactured in a manner that is itself known, e.g., by means of conventional mixing, dissolving, emulsifying, encapsulating, entrapping, or lyophilizing processes.

The compositions may be formulated in any of several ways. For example, the lightly-crosslinked polymer particles, the batimastat compound the osmotic pressure-adjusting salt and any of the optional ingredients also being used may be pre-blended, added to all or part of the water, and stirred vigorously until apparent polymer dispersion is complete, as evidenced by the absence of visible polymer aggregates, which usually occurs within about an hour. Sufficient pH adjusting agent is then added incrementally to reach the desired pH, and more water to reach 100 percent formula weight can be added at this time, if necessary.

Another convenient method involves adding the batimastat compound to about 95 percent of the final water volume and stirring for a sufficient time to saturate the solution. Solution saturation can be determined in a known manner, e.g., using a spectrophotometer. The lightly crosslinked polymer particles and the osmotic pressure-adjusting salt are first blended in dry form and then added to the drug-saturated suspension and stirred until apparent polymer hydration is complete. Following the incremental addition of sufficient pH adjusting agent to reach the desired pH, the remained of the water is added, with stirring, to bring the composition to 100 percent formula weight.

A preferred method of formulating the topical ophthalmic compositions of this invention involves adding the polymer to 90 grams of water per 100 grams of gel, then stirring for about 1 hour until the gel is fully hydrated. The batimastat compound is then added as an aqueous solution or a suspension, with stirring. Next, sodium chloride is added as a solid, together with sufficient water to bring the mass to 100 grams, and the pH is adjusted to the final pH, e.g., with 10N sodium hydroxide.

The prepared composition is then sterilized, preferably by briefly heating, e.g., for about 30 minutes with steam at about 121 degrees Celsius, and then filled into appropriate containers. Preservative-free compositions may be filled into unit-dose containers, at the preferred viscosity, eliminating the potential for preservative-related irritation and sensitization of the corneal epithelium, as has been observed to occur particularly from ophthalmic medicaments containing preservatives such as mercurial preservatives.

Compositions containing preservatives may also be filled into multiple-dose containers at the preferred viscosity, if desired, particularly because the viscosities of the compositions of this invention permit constant, accurate dosages to be administered dropwise to the eye as many times each day as necessary. In those compositions where preservatives are to be included, suitable preservatives include benzalkonium chloride in amounts ranging from about 0.001 to about 0.02 percent, chlorobutanol, preferably at about 0.5 percent, chlorobutanol chloral derivative, preferably at about 0.5 percent, methyl paraben and propyl paraben, preferably about 0.01 to about 0.05 percent, sorbic acid, preferably about 0.2 percent, Cetrimide, preferably about 0.01 percent, polyquat, preferably about 0.001 percent, cetyl bromide, preferably about 0.01 percent, and the like, each of the foregoing preservative amounts being based on the total weight of the composition.

EXAMPLE 2

Topical Ophthalmic Administration of a Composition Containing Batimastat in Mice A newborn mouse animal model of neovascularization conditions and diseases such as age-related macular degeneration, diabetic retinopathy, and oxygen-induced blindness demonstrates the utility and surprisingly advantageous topical, ophthalmic administration of batimastat.

Newborn mice on postnatal day 7 are kept in high oxygen (75 percent) from day 7 to 11, and then are brought to normal room air on day 12. A relative hyperoxia results, and retinal neovascularization is seen in 100 percent of the exposed animals by day 17. Some of the animals (n=9) initially exposed to the oxygen cycle receive Formulation 1 eyedrops four times a day in the right eye on days 14–17 (four days) (Group I). Some animals (n=9) receive the same eyedrops, administered similarly, on days 13–17. In another group of animals (n=9) (Group III), the eyedrops are instilled in the right eye and normal saline is instilled in the left eye (control). Animals are sacrificed on day 17. Newborn animals kept in room air only for 17 days may serve as controls.

Eye tissue is processed for paraffin embedding sections, which are stained for nuclei with DAPI (diamidinophenylindole). Sections can be examined under a fluorescence microscope and nuclei on the vitreous side of the inner limiting membrane of the retina, representing microvascular cells, are counted in each section using a masked protocol.

Numerous neovascular tufts may be seen protruding from the retina into the vitreous in animals exposed to hyperoxia (75 percent oxygen) followed by room air. Quantification reveals about 52.86 neovascular nuclei per section in experimental animals (without drug treatment) compared to controls (0.53 neovascular nuclei per section). Animals treated with Formulation 1 eyedrops show a decrease in neovascular nuclei by 27.8 percent (Group I), 38.3 percent (Group II) and 39.47 percent (Group III) respectively (FIG. 1).

Figure 2:
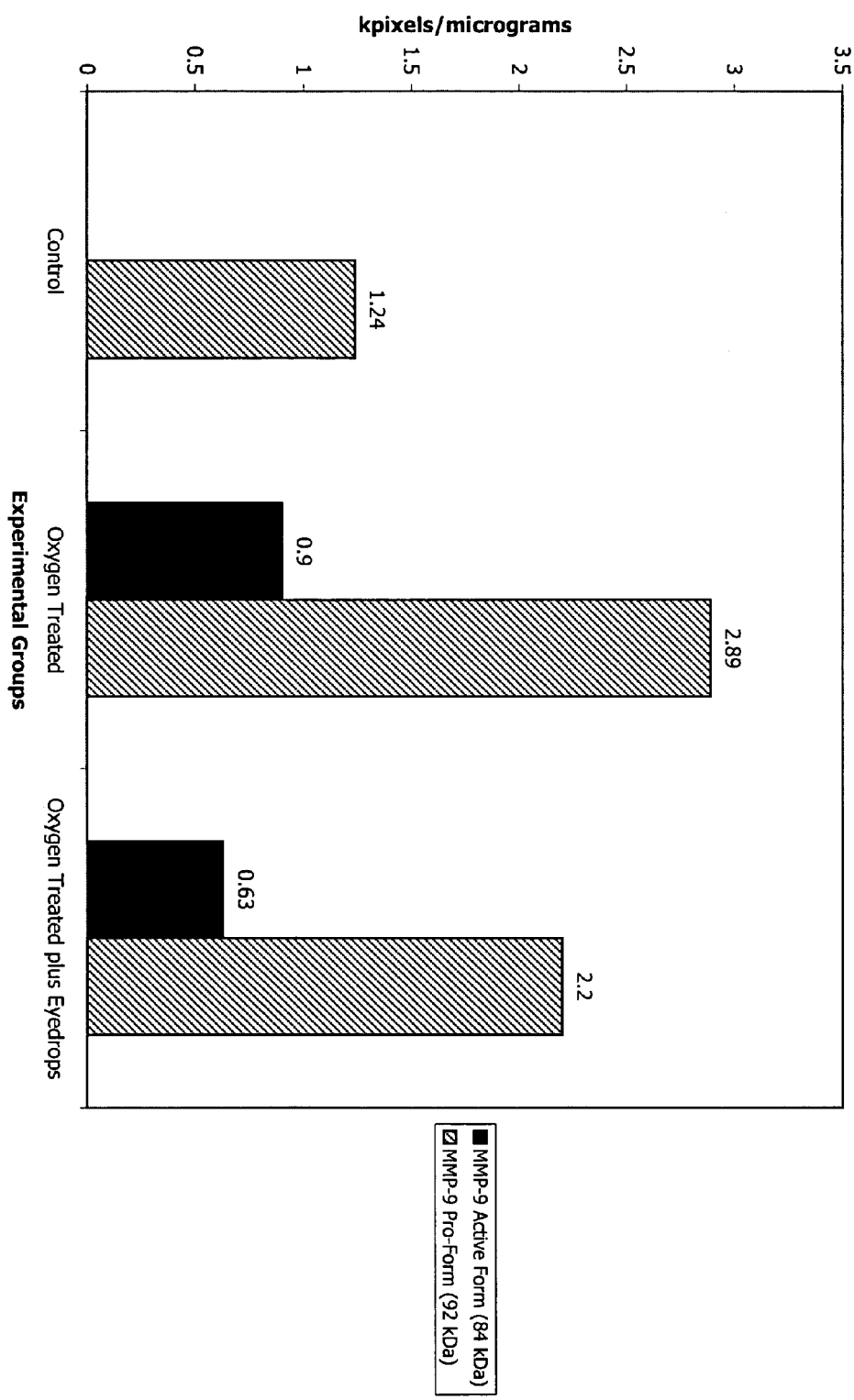
FIG. 2 depicts the relative levels of MMP-9 activity in control, hyperoxic untreated, and hyperoxic treated murine retinal tissue.
Figure 3:
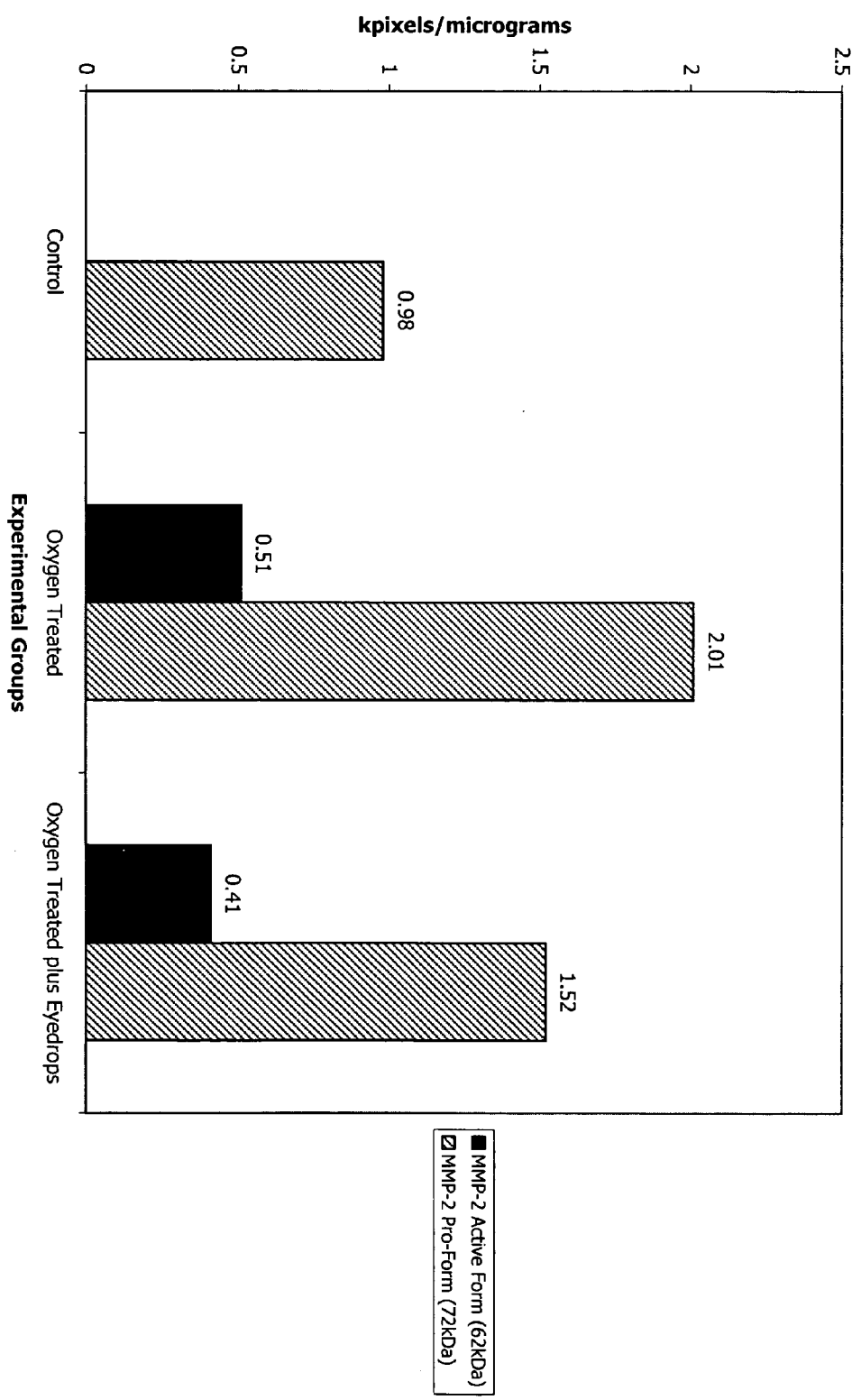
FIG. 3 depicts the relative levels of MMP-2 activity in control, hyperoxic untreated, and hyperoxic treated murine retinal tissue.

Analysis of MMP-2 activity in animals with retinal neovascularization shows a significant increase in the proform of MMP-2 (72 kDa) compared to controls (FIG. 2). The active form of MMP-2 (62 kDa), which is undetectable in controls, is also significantly increased in animals with neovascularization. The Formulation 1 eyedrops decrease the activity of both pro- and active forms of MMP-2. Analysis of MMP-9 activity in animals with retinal neovascularization shows a significant increase in the pro-form of MMP-9 (92 kDa) compared to controls (FIG. 3). The active form of MMP-9 (84 kDa), which is undetectable in controls, is significantly increased in animals with retinal neovascularization. Treatment with Formulation 1 eyedrops decreases the activity of both pro- and active forms of MMP-9 significantly. Animals with retinal neovascularization also show a significant increase in both the 32 kD and 54 kD molecular weight forms of urokinase compared to controls. Zymographic analysis does not show any change in activity of either form of urokinase in animals treated with Formulation 1 eyedrops (FIG. 4).

In another study, animals are treated with hyperoxia conditions, as described above. Then, batimastat is introduced into the animals via intraperitoneal injection (IP). A course of IP injection on days 12, 14 and 16 results in a 72 percent reduction in neovascularization in the same animal model (Das et al., Archives of Ophthalmology, 117:498–503 (1999)).

Figure 4:
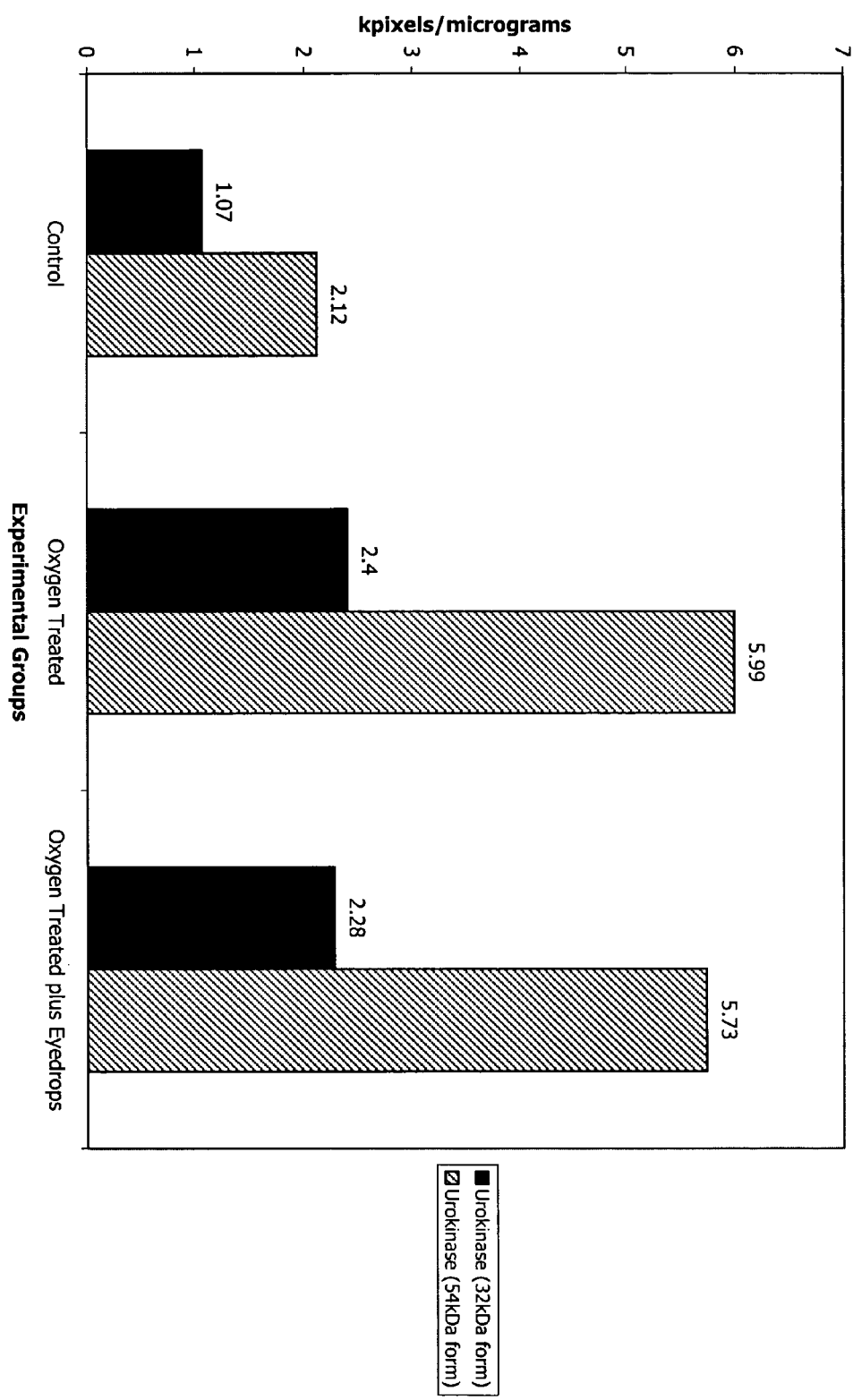
FIG. 4 depicts the relative levels of urokinase activity in control, hyperoxic untreated, and hyperoxic treated murine retinal tissue.

The result of Formulation 1 eyedrop formulation on the inhibition of retinal neovascularization is significant and the effect is specific to MMP inhibition, as shown by zymographic analysis and urokinase assays (FIG. 4). These results also show that the drug effectively reaches the retinal tissue and, thus, can be used to treat the retina via topical delivery.

EXAMPLE 3

Topical Ophthalmic Administration of a Composition Containing Batimastat in Rabbits A study in rabbits will examine the $^{14}C$ activity in ocular tissues and blood plasma following administration of a topical ophthalmic composition containing 0.3 percent labeled batimastat in the DuraSite® delivery vehicle. The ocular tissues to be examined are the aqueous humor, cornea, iris and ciliary body, vitreous humor, retina and choroid, and the sclera. The study will proceed in three step-wise phases: phase 1 will examine $^{14}C$ activity at 20 minutes, 40 minutes, 1 hour and 2 hours post-administration, phase 2 will examine $^{14}C$ activity at 3 and 4 hours post-administration, and phase 3 will examine $^{14}C$ activity at 6 and 8 hours post-administration. Initially, 6 rabbits (12 eyes) will be examined at each time point. If any phase of the study is not executed, the rabbits allocated to that phase may be reassigned to other time points to better estimate bioavailability and pharmacokinetics. Nor more than 12 rabbits will be assigned to any single time point. It is anticipated that 48–54 total rabbits will be used in the study. To control bias, animals will be randomly enrolled in the study. Within an animal room (total capacity 54 rabbits), each rabbit eligible for enrollment in the study will be randomly assigned a temporary sequential number. Rabbits will then be selected for use in the study in sequential order of temporary number.

This study will use 48–54 female New Zealand White rabbits that weigh approximately 1.8 to 2.8 kg upon arrival and will be approximately 9 weeks old. Each rabbit will be identified with an ear tag bearing a unique number, and the rabbit's cage will also bear the same number. Rabbits will be acclimated to the laboratory environment in a specified quarantine area for a minimum of two weeks before being used in the study. Rabbits will receive a daily ration of commercially available feed and tap water ad libitum. Rabbit health will be monitored daily. Rabbits will be placed in temporary housing after instillation of $^{14}C$-labeled test material. The rabbits will be anesthetized and euthanized at the conclusion of the in vivo experimental period.

The test material will be administered with a positive displacement micropipettor. The average mass and standard deviation of dispensed test material will be estimated. Approximately 25 mg of test material will be instilled into the lower cul-de-sac of both eyes. The material will be placed into the eye by gently pulling the lower lid away from the globe to form a cup into which the material will be instilled.

Rabbits will be anesthetized with an intramuscular injection of ketamine and xylazine (0.4 ml/kg each) approximately 20 minutes prior to the scheduled collection time of aqueous humor. Aqueous humor will be collected from both eyes according to methods known in the art. Aqueous humor will be collected from OD, then OS. A 0.5 ml syringe with a fixed 28 G×½" needle will be used, and an ophthalmic solution of 0.5 percent proparacaine hydrochloride will be administered prophylactically to all eyes without testing for corneal reflex. Eyes will be irrigated with commercially available Eye Irrigating Solution. Both eyes will be enucleated starting with OD. Tissues collected will include: bulbar conjunctiva, cornea, iris, sclera, vitreous humor, and retina. Tissues will be placed into preweighed scintillation vials. All scintillation vials will be capped and weighed. Immediately after the aqueous humor has been collected from both eyes, approximately 5 ml of blood will be withdrawn by intracardiac puncture. Blood will be collected into a heparinized tube.

For the bulbar conjunctiva, cornea, iris, sclera and retina/choroid, 100 µl of reverse osmosis (RO) purified water will be added to each sample and the sample vortexed. 250 µl of hyamine hydroxide will be added to each vial and the sample again vortexed. The samples will then be incubated at 55 degrees Celsius in a water bath until solubilized (approximately 1–4 hours). After solubilization is complete, the samples will again be vortexed, and 6 ml of CytoScintES® scintillation cocktail will be added to each sample. Solubilized samples will be immediately mixed with the scintillation cocktail by repeatedly inverting the capped vial. Vigorous shaking will be avoided.

For the vitreous humor, 100 µl of reverse osmosis (RO) purified water will be added to each sample and the sample vortexed. 750 µl of hyamine hydroxide will be added to each vial and the sample again vortexed. The samples will then be incubated at 55 degrees Celsius in a water bath until solubilized. After solubilization is complete, the samples will again be vortexed, and approximately 18 ml of CytoScintES® scintillation cocktail will be added to each sample. Solubilized samples will be immediately mixed with the scintillation cocktail by repeatedly inverting the capped vial. Vigorous shaking will be avoided.

For the aqueous humor, 6 ml of CytoScintES® scintillation cocktail will be added directly to each aqueous humor sample and mixed by repeatedly inverting the capped vial. There is not need to solubilize the aqueous humor sample. Blood samples will be kept in a cooler containing ice packs to keep them cold until separation. Plasma will be separated from the red blood cells by centrifugation at 4 degrees Celsius and 1200–1500 g for 15 minutes. Immediately after centrifuging, 1 ml of the plasma will be pipetted from the tube and placed into a 20 ml scintillation vial. 18 ml of CytoScintES® scintillation cocktail will be added directly to each plasma sample and mixed by repeatedly inverting the capped vial. All samples will be dark-adapted overnight before counting in a Beckman LS 3801.

Figure 5:
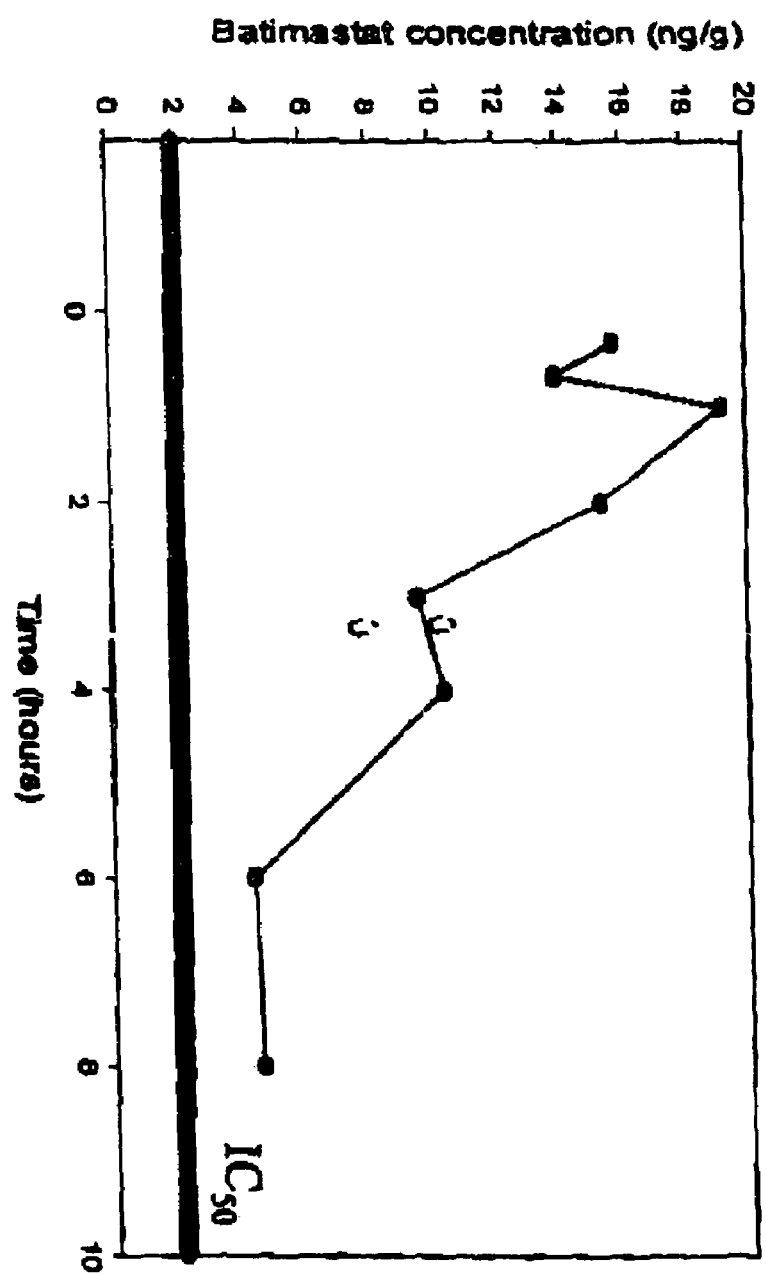
FIG. 5 depicts the retinal tissue levels of batimastat over time following topical application to rabbit eyes.

The topical batimastat composition reaches the retinal tissue shortly after topical administration to the eye, and is maintained in the retinal tissue at therapeutically effective levels for at least 8 hours, as shown in FIG. 5. These results show that the drug effectively reaches the retinal tissue and thus can be used to treat the retina via topical delivery.

All publications and patents mentioned in the above specification are herein incorporated by reference. The above description, drawings and examples are only illustrative of preferred embodiments which achieve the objects, features and advantages of the present invention. It is not intended that the present invention be limited to the illustrative embodiments. Any modification of the present invention which comes within the spirit and scope of the following claims should be considered part of the present invention.

What is claimed is:

1. A method for treating retinal neovascularization in a mammal in need of such treatment, comprising topically administering to the eye a composition capable of delivering a therapeutically effective amount of a compound of formula I to the retina, said composition comprising a polymeric suspension agent which suspends a therapeutic neovascularization inhibitory agent, said therapeutic agent consisting essentially of a compound in the group of formula I:

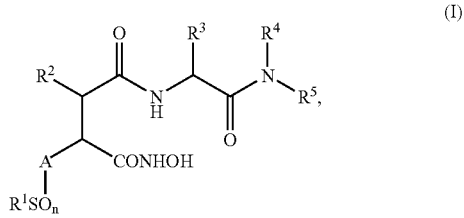

where $R^1$ represents thienyl, $R^2$ represents a hydrogen atom or a $C_1$–$C_6$ alkyl, $C_1$–$C_6$ alkenyl, phenyl($C_1$–$C_6$) alkyl, cycloalkyl($C_1$–$C_6$)alkyl or cycloalkenyl($C_1$–$C_6$)alkyl group, $R^3$ represents an amino acid side chain or a $C_1$–$C_6$ alkyl, benzyl, ($C_1$–$C_6$ alkoxyl)benzyl or benzyloxy($C_1$–$C_6$ alkyl) or benzyloxy benzyl group, $R^4$ represents a hydrogen atom or a $C_1$–$C_6$ alkyl group, $R^5$ represents a hydrogen atom or a methyl group, n is an integer having the value 0, 1 or 2, and A represents a $C_1$–$C_6$ hydrocarbon chain, optionally substituted with one or more $C_1$–$C_6$ alkyl, phenyl or substituted phenyl groups, or a salt thereof; and a derivative of batimastat formed by methylation halogenation, acetylation, esterification and hydroxylation.

2. The method of claim 1, wherein said mammal is a human.

3. The method of claim 1, wherein said compound of formula I is batimastat.

4. The method of claim 1, wherein said polymeric suspension agent comprises polycarbophil.

5. The method of claim 4, wherein said polycarbophil is present at a concentration of about 0.5 to about 1.5 percent by weight.

6. The method of claim 1, wherein said composition also contains one or more pharmaceutically acceptable carriers, excipients, gels, solutions, diluents preservatives, stabilizers, chelating agents, dyes, antibiotics, antimicrobials, or anti-fungal agents.

7. The method of claim 1, wherein said compound of formula I is present from about 0.01 to about 3 percent, by weight of said composition.

8. The method of claim 7, wherein said polycarbophil is present at a concentration of about 0.5 to about 1.5 percent by weight.

9. The method of claim 8, wherein said compositions also contains one or more pharmaceutically acceptable carriers, excipients, gels, solutions, diluents preservatives, stabilizers, chelating agents, dyes, antibiotics, antimicrobials, or anti-fungal agents.

10. The method of claim 1, wherein said compound is not batimastat.

11. The method of claim 1, wherein said mammal in need of such treatment suffers from diabetic retinopathy, age-related macular degeneration, neovascular glaucoma, retinopathy of prematurity, sickle-cell retinopathy, retinal vein occlusion, oxygen induced retinopathy, neovascularization due to ocular insults, neovascularization due to ocular trauma, or neovascularization due to surgical injury or surgical transplantation of eye tissue.

12. The method of claim 1, wherein said mammal in need of such treatment suffers from a disease or condition where a part of the retina is subject to:
   a relatively non-perfused state compared to surrounding tissue;
   a disease or condition where any one or more of the proteins, proteinases, hormones, or cellular signals associated with angiogenesis are detected;
   a disease or condition where new vessel growth can be detected or observed; or
   a disease associated with matrix metalloproteinase activity, endothelial invasion.

13. A method for inhibiting retinal neovascularization in a mammal with a disease or condition associated with the manifestation of retinal neovascularization, comprising topically administering to the eye a composition capable of delivering a therapeutically effective amount of a compound of formula I to the retina, said composition comprising a polymeric suspension agent which suspends a therapeutic neovascularization inhibitory agent, said therapeutic agent consisting essentially of a compound in the group of formula I:

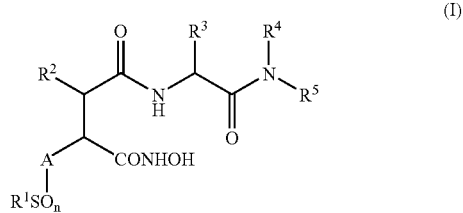

where $R^1$ represents thienyl, $R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl or cycloalkenyl($C_1$–$C_6$)alkyl group, $R^3$ represents an amino acid side chain or a $C_1$–$C_6$ alkyl, benzyl, ($C_1$–$C_6$ alkoxyl)benzyl or benzyloxy($C_1$–$C_6$ alkyl) or benzyloxy benzyl group, $R^4$ represents a hydrogen atom or a $C_1$–$C_6$ alkyl group, $R^5$ represents a hydrogen atom or a methyl group, n is an integer having the value 0, 1 or 2, and A represents a $C_1$–$C_6$ hydrocarbon chain, optionally substituted with one or more $C_1$–$C_6$ alkyl, phenyl or substituted phenyl groups, or a salt thereof; and a derivative of batimastat formed by methylation halogenation, acetylation, esterification and hydroxylation.

14. The method of claim 13, wherein said mammal is a human.

15. The method of claim 13, wherein said compound of formula I is batimastat.

16. The method of claim 13, wherein said polymeric suspension agent comprises polycarbophil.

17. The method of claim 16, wherein said polycarbophil is present at a concentration of about 0.5 to about 1.5 percent by weight.

18. The method of claim 13, wherein said composition also contains one or more pharmaceutically acceptable carriers, excipients, gels, solutions, diluents preservatives, stabilizers, chelating agents, dyes, antibiotics, antimicrobials, or anti-fungal agents.

19. The method of claim 13, wherein said compound of formula I is present from about 0.01 to about 3 percent, by weight of said composition.

20. The method of claim 19, wherein said polycarbophil is present at a concentration of about 0.5 to about 1.5 percent by weight.

21. The method of claim 20, wherein said compositions also contains one or more pharmaceutically acceptable carriers, excipients, gels, solutions, diluents preservatives, stabilizers, chelating agents, dyes, antibiotics, antimicrobials, or anti-fungal agents.

22. The method of claim 13, wherein the mammal's condition or disease associated with the manifestation of retinal neovascularization is diabetic retinopathy, age-related macular degeneration, glaucoma, retinopathy of prematurity, sickle-cell retinopathy, retinal vein occlusion, oxygen induced retinopathy, ocular insults, ocular trauma, or surgical injury or surgical transplantation of eye tissue.

23. The method of claim 13, wherein the mammal's condition or disease associated with the manifestation of retinal neovascularization is a disease or condition where a part of the retina is subject to:
a relatively non-perfused state compared to surrounding tissue;
a disease or condition where any one or more of the proteins, proteinases, hormones, or cellular signals associated with angiogenesis are detected;
a disease or condition where new vessel growth can be detected or observed; or
a disease associated with matrix metalloproteinase activity, endothelial invasion.

24. A method for treating or inhibiting retinal neovascularization in a mammal in need of treatment or with a disease or condition associated with the manifestation of retinal neovascularization, comprising topically administering to the eye a composition capable of delivering a therapeutically effective amount of a compound of formula I to the retina, said composition comprising a polymeric suspension agent which suspends a neovascularization inhibitory agent, said agent consisting of a compound in the group of formula I:

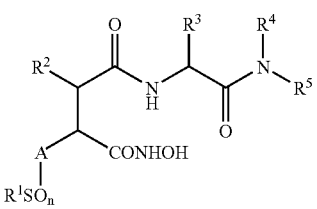

(I)

where $R^1$ represents thienyl, $R^2$ represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl or cycloalkenyl($C_1$–$C_6$)alkyl group, $R^3$ represents an amino acid side chain or a $C_1$–$C_6$ alkyl, benzyl, ($C_1$–$C_6$ alkoxyl)benzyl or benzyloxy($C_1$–$C_6$ alkyl) or benzyloxy benzyl group, $R^4$ represents a hydrogen atom or a $C_1$–$C_6$ alkyl group, $R^5$ represents a hydrogen atom or a methyl group, n is an integer having the value 0, 1 or 2, and A represents a $C_1$–$C_6$ hydrocarbon chain, optionally substituted with one or more $C_1$–$C_6$ alkyl, phenyl or substituted phenyl groups, or a salt thereof; and a derivative of batimastat formed by methylation halogenation, acetylation, esterification and hydroxylation; said composition further comprising one or more pharmaceutically acceptable carriers, excipients, gels, solutions, diluents preservatives, stabilizers, chelating agents, dyes, antibiotics, antimicrobials, or anti-fungal agents.

25. The method of claim 24, wherein said mammal is a human.

26. The method of claim 24, wherein said compound of formula I is batimastat.

27. The method of claim 24, wherein said polymeric suspension agent comprises polycarbophil.

28. The method of claim 27, wherein said polycarbophil is present at a concentration of about 0.5 to about 1.5 percent by weight.

29. The method of claim 24, wherein said compound of formula I is present from about 0.01 to about 3 percent, by weight of said composition.

30. The method of claim 29, wherein said polycarbophil is present at a concentration of about 0.5 to about 1.5 percent by weight.

31. The method of claim 24, wherein said compound of formula I is not batimastat.

32. The method of claim 24, wherein said mammal is one which suffers from diabetic retinopathy, age-related macular degeneration, glaucoma, retinopathy of prematurity, sickle-cell retinopathy, retinal vein occlusion, oxygen induced retinopathy, ocular insults, ocular trauma, surgical injury, or surgical transplantation of eye tissue.

33. The method of claim 24, wherein said mammal is one with a disease or condition where a part of the retina is subject to:
a relatively non-perfused state compared to surrounding tissue;
a disease or condition where any one or more of the proteins, proteinases, hormones, or cellular signals associated with angiogenesis are detected;
a disease or condition where new vessel growth can be detected or observed; or
a disease associated with matrix metalloproteinase activity, endothelial invasion.

34. A method for treating retinal neovascularization in a mammal in need of treatment, comprising topically administering to the eye a composition capable of delivering a therapeutically effective amount of a compound of formula I to the retina, said composition consisting of a polymeric suspension agent and a compound in the group of formula I:

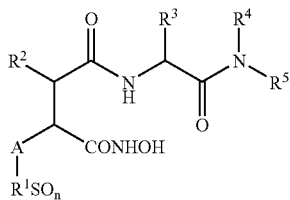

(I)

where R¹ represents thienyl, R² represents a hydrogen atom or a $C_1$–$C_6$ alkyl, $C_1$–$C_6$ alkenyl, phenyl($C_1$–$C_6$)alkyl, cycloalkyl($C_1$–$C_6$)alkyl or cycloalkenyl($C_1$–$C_6$)alkyl group, R³ represents an amino acid side chain or a $C_1$–$C_6$ alkyl, benzyl, ($C_1$–$C_6$ alkoxyl)benzyl or benzyloxy($C_1$–$C_6$ alkyl) or benzyloxy benzyl group, R⁴ represents a hydrogen atom or a $C_1$–$C_6$ alkyl group, R⁵ represents a hydrogen atom or a methyl group, n is an integer having the value 0, 1 or 2, and A represents a $C_1$–$C_6$ hydrocarbon chain, optionally substituted with one or more $C_1$–$C_6$ alkyl, phenyl or substituted phenyl groups, or a salt thereof; and a derivative of batimastat formed by methylation halogenation, acetylation, esterification and hydroxylation; and one or more pharmaceutically acceptable carriers, excipients, gels, solutions, diluents preservatives, stabilizers, chelating agents, dyes, antibiotics, antimicrobials, or anti-fungal agents.

35. The method of claim 34, wherein said mammal is a human.

36. The method of claim 34, wherein said compound of formula I is batimastat.

37. The method of claim 34, wherein said polymeric suspension agent comprises polycarbophil.

38. The method of claim 37, wherein said polycarbophil is present at a concentration of about 0.5 to about 1.5 percent by weight.

39. The method of claim 34, wherein said compound of formula I is present from about 0.01 to about 3 percent, by weight of said composition.

40. The method of claim 39, wherein said polycarbophil is present at a concentration of about 0.5 to about 1.5 percent by weight.

41. The method of claim 34, wherein said compound of formula I is not batimastat.

42. The method of claim 34, wherein said mammal in need of such treatment suffers from diabetic retinopathy, age-related macular degeneration, neovascular glaucoma, retinopathy of prematurity, sickle-cell retinopathy, retinal vein occlusion, oxygen induced retinopathy, neovascularization due to ocular insults, neovascularization due to ocular trauma, or neovascularization due to surgical injury or surgical transplantation of eye tissue.

43. The method of claim 34, wherein said mammal in need of such treatment suffers from a disease or condition where a part of the retina is subject to:
  a relatively non-perfused state compared to surrounding tissue;
  a disease or condition where any one or more of the proteins, proteinases, hormones, or cellular signals associated with angiogenesis are detected;
  a disease or condition where new vessel growth can be detected or observed; or
  a disease associated with matrix metalloproteinase activity, endothelial invasion.

* * * * *